United States Patent [19]

D'Angelo et al.

[11] Patent Number: 5,286,509
[45] Date of Patent: Feb. 15, 1994

[54] L-ASPARTYL-D-ALPHA-AMINOALKAN-OYL-(S)-N-ALPHA-ALKYLBENZYL AMIDES USEFUL AS ARTIFICIAL SWEETENERS

[75] Inventors: Lihong L. D'Angelo, Decatur; James G. Sweeny, Atlanta, both of Ga.

[73] Assignee: The Coca-Cola Company, Atlanta, Ga.

[21] Appl. No.: 902,310

[22] Filed: Jun. 22, 1992

[51] Int. Cl.$^5$ .................. A23L 1/236; C07C 229/00
[52] U.S. Cl. .............................. 426/548; 562/450
[58] Field of Search ...................... 562/450; 426/548

[56] References Cited

U.S. PATENT DOCUMENTS

| | | |
|---|---|---|
| 4,411,925 | 10/1983 | Brennan et al. |
| 4,564,528 | 1/1986 | Saltzman et al. |
| 4,677,126 | 6/1987 | Janusz et al. |
| 4,692,512 | 9/1987 | Janusz |
| 4,761,495 | 8/1988 | Wirth et al. |

OTHER PUBLICATIONS

Zeng, et al., "In Pursuit of a Better Sweetner," J. Agric. Food Chem. 39, 782–85.
Y. Ariyoshi, "Structure—Taste Relationships of Aspartyl Tripeptide Esters" Bull. Chem. Soc. Japan, 57, 3197 (1984).

*Primary Examiner*—Joseph Golian
*Attorney, Agent, or Firm*—Kenyon & Kenyon

[57] ABSTRACT

The present invention relates to L-aspartyl-D-α-aminoalkanoyl-(S)-N-α-alkylbenzyl amides that are useful as artificial sweetener compounds. In particular, the present invention relates to compositions containing L-aspartyl-D-α-aminobutyric acid-(S)-α-ethylbenzyl amide and L-aspartyl-D-valine-(S)-α-ethylbenzyl amide as artificial sweetener compounds having very high sweetness potency.

30 Claims, No Drawings

L-ASPARTYL-D-ALPHA-AMINOALKANOYL-(S)-N-ALPHA-ALKYLBENZYL AMIDES USEFUL AS ARTIFICIAL SWEETENERS

FIELD OF THE INVENTION

This invention relates to artificial sweetener compounds comprising L-aspartyl-D-α-aminoalkanoyl-(S)-N-α-alkylbenzyl amides.

BACKGROUND OF THE INVENTION

L-aspartyl-D-alanine-N-alkyl amides, such as disclosed in U.S. Pat. No. 4,411,925, are known to be useful as artificial sweeteners:

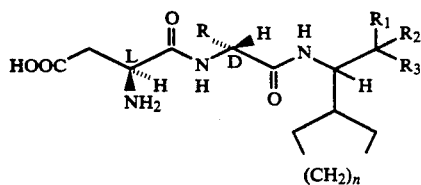

In the series of compounds described by the above structure, the most potent material reported was the L-aspartyl-D-alanine amide of (+/−) t-butyl-cyclopropyl methylamine ($R_1=R_2=R_3=CH_3$, n=0; wherein the sweetness potency (SP) was reported to be 1200 times sucrose.) It was furthermore emphasized that the nature of R in the above structure was important for sweetness potency, with $R=CH_3$ (D-alanine) being especially preferred. In the typical case of the L-aspartyl-D-alanine amides having the structure,

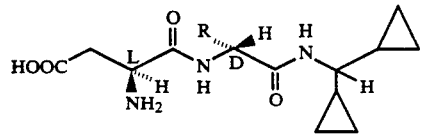

the sweetness potency decreases as R is increased, that is, for R=methyl, SP=1200, for R=ethyl, SP=500, and for R=isopropyl, SP=110.

Zeng et al., J. Agric. Food Chem. 39, 782-85 (1991), disclose L-aspartyl-D-alanine-N-phenyl amides wherein the benzene ring may have methyl-substituents:

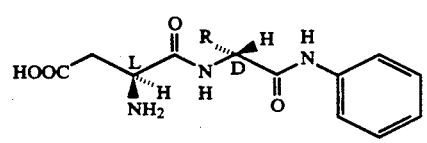

These compounds may be described as aniline amides of L-aspartyl-D-alanine. The individual members of this family of aniline amides were disclosed to have a sweetness potency that was at most 75 times that of sucrose except for the highly substituted 2,6-dimethylaniline amide which was disclosed to have a sweetness potency 500 times the sweetness of sucrose. In addition to the relatively low sweetness potency of most of the individual members of this aniline-based series of compounds, these compounds have a potential for toxicity that is known for aniline derivatives.

In addition, Ariyoshi, Bull. Chem. Soc. Japan, 57, 3197 (1984), discloses a series of L-aspartyl-D-alanyl-α-amino acid esters and L-aspartyl-D-valinyl-α-amino acid esters that are tasteless, bitter or of sweetness potency less than 50 times sucrose.

OBJECTS AND SUMMARY OF THE INVENTION

An object of the present invention is to provide useful chemically stable artificial sweeteners having high sweetness potency using economic, safe and convenient reaction materials.

Another object of the present invention is to provide artificial sweeteners having high heat stability at temperatures typically used for preparing foods.

The present invention provides an artificial sweetener compound comprising an L-aspartyl-D-α-aminoalkanoyl-(S)-α-alkylbenzyl amide having the structure:

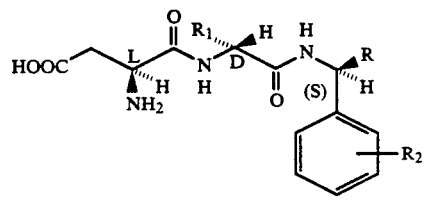

wherein
$R_1=H$, $-CH_3$, $-CH_2CH_3$, $-CH_2CH_2CH_3$, $-CH(CH_3)_2$, $-C(CH_3)_3$, $-CH_2OCH_3$, $-CH_2OH$ or phenyl
wherein
$R_2=H$ or $CH_3$;

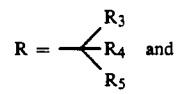

$R_3$, $R_4$ and $R_5=H$, $-CH_3$ or $-CH_2CH_3$; or

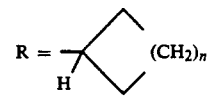

wherein n=0, 1, 2, 3, 4.

DETAILED DESCRIPTION OF THE INVENTION

The methods by which the objects, features and advantages of the present invention are achieved will now be described in more detail. These particulars provide a more precise description of the invention for the purpose of enabling one skilled in the art to practice the invention, but without limiting the invention to the specific embodiments described.

The L-aspartyl-D-amino acid amides of the present invention may be conveniently obtained by preparing a dipeptide using any of several known methods for the coupling of amino acids, (e.g., M. Bodansky, *Principles of Peptide Synthesis*, Berlin, (1984), Springer Verlag), and then coupling the dipeptide with an amine to produce the desired amide.

For example, the method outlined below has been found useful, where $R_1$ and $R_2$ are alkyl groups.

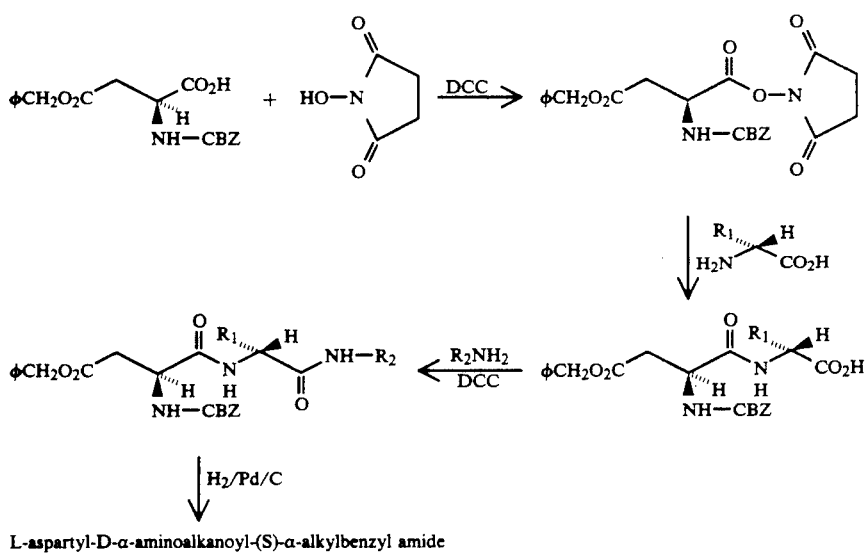

In the first step of the above reaction sequence, a diprotected aspartic acid is condensed with N-hydroxysuccinimide to afford activated aspartyl-N-hydroxy succinimide ester. In this case the diprotected aspartic acid is a B-benzyl-N-carbobenzyloxy ("CBZ") derivative which is commercially available. Condensation of the CBZ-derivative with hydroxysuccimide is achieved by use of dicyclohexylcarbodiimide (DCC) as the coupling agent. The DCC coupling agent is also readily available from known commercial sources.

In the second step, the activated aspartylsuccinimide ester may be reacted with an appropriate D-amino acid in dioxane-water with triethylamine to produce the $\beta$-benzyl-N-carbobenzyloxy-L-aspartyl-D-amino acid. The preferred D-amino acids include D-alanine, D-valine, D-$\alpha$-aminobutyric acid, D-phenylglycine and D-$\alpha$-aminopentanoic acid. The most preferred D-amino acids of this invention are D-alanine, D-$\alpha$-aminobutyric acid and D-valine.

In the third step the reaction product of the second step may be activated with DCC and coupled in dioxane with an appropriate amine to afford the $\beta$-benzyl-N-carbobenzyloxy-L-aspartyl-D-amino acid amide. The preferred amines of this invention include amines such as $\alpha$-methylbenzyl amine, $\alpha$-ethylbenzyl amine, $\alpha$-isopropylbenzyl amine, $\alpha$-t-butylbenzyl amine, $\alpha$-n-propylbenzyl amine, $\alpha$-phenylbenzyl amine, $\alpha$-cyclopropyl benzyl amine, and $\alpha$-iso-butylbenzyl amine. The (S)-enantiomer or a racemic mixture of these amines may be used. Preferably the (S)-enantiomer is used. The most preferred amine of this invention is (S)-$\alpha$-ethyl-benzyl amine. In the final step the sweetener compound is obtained by deprotection of the product of the third step by catalytic hydrogenation in an alcoholic solvent using Pd/C as catalyst.

While the above method has proven convenient and was used in preparation of all of the compounds described in the examples that follow, other methods may be envisioned which could prove equally advantageous. For example, as described in U.S. Pat. No. 4,411,925, activation of the acid groups of the first and third steps could be achieved using an alkyl chloroformate and a tertiary amine base in place of the DCC. In addition, the use of other protecting groups for the aspartic acid moiety, such as the combination of B-t-butyl ester and N-t-butoxycarbonyl can be envisioned. In this case, deprotection in step 4 would require acid catalysis rather than catalytic hydrogenation.

A second preferred method for preparation of compounds of this invention involves coupling of an N-protected $\alpha$-amino acid with (S)-alkyl benzylamine ($R_2NH_2$) as a first step, as shown, wherein $R_1$ and $R_2$ are alkyl groups:

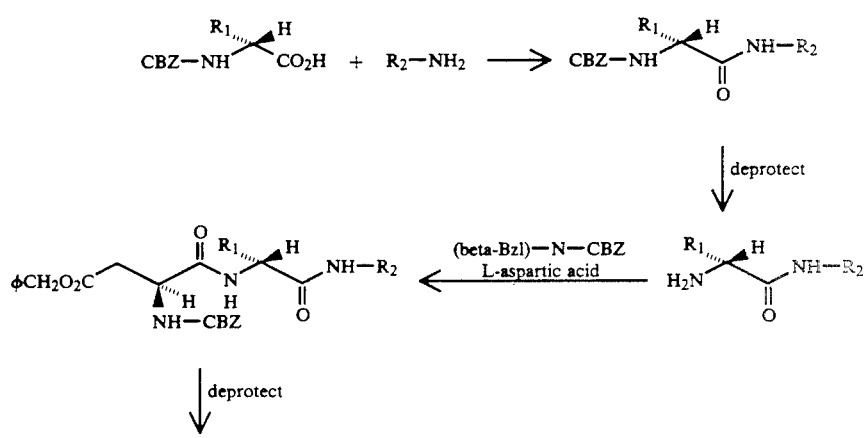

L-aspartyl-D-α-aminoalkanoyl-(S)-α-alkylbenzyl amide

In the second step the protecting group is removed. In the case of a carbobenzyloxy (CBZ) group the protecting group is removed by catalytic hydrogenation. This new amine is then reacted in a third step with N-carbobenzyloxy-β-benzyl-L-aspartic acid and a condensing agent such as DCC to produce a N-carbobenzyloxy-β-benzyl aspartyl-D-amino acid (S)-α-alkylbenzyl amide. The sweetener product is then obtained in a fourth step by catalytic removal of the protecting groups using known methods of hydrogenation over Pd/C catalyst.

As in the first method, other aspartic acid protecting groups such as the t-butyl ester and the N-t-butoxy carbonyl group may be used. Other acid activating reagents such as an alkyl chloroformate and a tertiary amine base may be used in place of DCC.

Still another modification of the second method would involve replacement of the N-carbobenzyloxy-β-benzyl aspartic acid of the third step with an N-protected aspartic anhydride such as the N-carbobenzyloxy- or the N-CHO analogues. Deprotection could then be carried out using hydrogenation over Pd/C in the case of an N-carbobenzyloxy-group or aqueous acid in the case of an N-CHO group. Coupling of amines with aspartic anhydrides usually gives some of the unwanted β-aspartyl amides, but they can be removed from the final product by fractional crystallization. For use of N-carbobenzyloxy-aspartic anhydride, see C. P. Yang and C. S. Su, *J. Org. Chem.* 51 5186 (1986). For the N-CHO aspartic anhydride, see U.S. Pat. Nos. 3,879,372 or 3,933,781.

The α-alkylbenzylamines used with the present invention are known in the prior art, and may be prepared by reduction of the corresponding ketoxime with sodium in ethanol. The ketoximes may be obtained from the corresponding ketones, which are commercially available. The amines used in the examples had boiling points corresponding to literature values and $^1$H and $^{13}$C NMR spectra consistent with their assigned structures.

Except for the case of the (R)-α- and (S)-α-methylbenzylamines which were purchased as such, the α-alkylbenzyl amines were prepared as racemic mixtures. One of the synthetic amines, the α-ethylbenzylamine, was resolved and resulted in a showing that predominantly the (S)-isomer invokes sweetness. Resolution was achieved by five recrystallizations of the L-(+)-tartaric acid salt of the racemic amine from 95% ethanol.

The other materials, the N-carbobenzyloxy-β-benzyl aspartic acid, the hydroxysuccinimide, the dicyclohexylcarbodiimide (DCC), and the D-amino acids, including D-alanine, D-valine, D-α-aminobutyric acid, D-phenylglycine acid and D-α-aminopentanoic acid are all readily available commercially.

The results of the sweetness potency measurements for the disclosed sweeteners of this invention are summarized in Tables 1-4. The sweetness potency was determined by having four tasters compare the sweetness of various dilutions of the test compound with a 200 ppm equivalent solution of aspartame, wherein the sweetness of aspartame was taken to be 180 times sucrose.

For the L-aspartyl-D-α-aminoalkanoyl-(S)-N-α-alkylbenzyl amides, the presence of the benzyl group, which is novel in itself, produces a high sweetness potency for the various analogues. For example, the results in Table 1 show an increased sweetnesss potency for the S-enantiomer over the R-enantiomer and a high sweetness potency for the (R,S) mixtures of ethyl-, propyl- and t-butyl- α-alkylbenzyl substituents as well as for the compound having an additional phenyl group at the α-benzyl position. Furthermore, contrary to the compounds of U.S. Pat. No. 4,411,925, the data presented in Table 2 generally indicate that increasing the size of the $R_1$ group of the chemical structure shown in Table 2 results in an increase in the sweetness potency. However, the n-propyl-group derivative was found to be less sweet than the methyl-, ethyl- or isopropyl-group derivatives, showing that there are limits on the size of $R_1$.

The combination of the highest potency of D-amino acid from Table 2, valine, with the highest potency of α-alkylbenzyl substituent from Table 1, (S)-α-ethylbenzyl, might be expected to produce a compound having the highest overall sweetness potency. Indeed, Table 3 shows that L-aspartyl-D-valine-(S)-N-α-ethylbenzyl amide has a sweetness potency of 1500 times sucrose. However, Table 3 shows an unexpectedly higher sweetness potency of 2500 times sucrose for L-aspartyl-D-α-aminobutyric-acid-(S)-N-α-alkylbenzyl amide. The results in Table 3, thus, indicate L-aspartyl-D-α-aminobutyric-acid-(S)-N-α-alkylbenzyl amide and L-aspartyl-D-valine-(S)-N-α-ethylbenzyl amide to be the most preferred sweeteners of the present invention.

The results in Table 4 show that methylation of the aromatic ring of the benzyl group produces a decrease in sweetness potency for each of the compounds shown.

TABLE 1

Effect of amine structure upon the sweetness potency of (L)-aspartyl-(D)-alanine amides.

| $R_2$ | SP (× Sucrose) |
|---|---|
| —CH$_3$ (S) | 180 |
| —CH$_3$ (R) | <10 |
| —CH$_2$CH$_3$ (R,S) | 270 |
| —CH(CH$_3$)$_2$ (R,S) | 180 |
| —CH$_2$CH$_2$CH$_3$ (R,S) | 135 |
| —C(CH$_3$)$_3$ (R,S) | 150 |

TABLE 1-continued

Effect of amine structure upon the sweetness potency of (L)-aspartyl-(D)-alanine amides.

(L)—asp—N(H)—C(H)(CH₃)—C(=O)—N(H)—C(H)(H)(R₂) [D center; benzyl-type]

| R₂ | SP (× Sucrose) |
|---|---|
| phenyl | 180 |

TABLE 2

Effect of the (D)-amino acid structure upon the sweetness potency of the (L)-aspartyl-(D)-amino acid (S)-α-methyl benzyl amides.

(L)—asp—N(H)—C(R₁)(H)—C(=O)—N(H)—C(CH₃)(H)(phenyl) (S)

| R₁ | SP (× Sucrose) |
|---|---|
| —CH₃ | 180 |
| —CH₂CH₃ | 360 |
| —CH₂CH₂CH₃ | 90 |
| —CH(CH₃)₂ | 540 |
| —phenyl | 270 |

TABLE 3

Effect of the variation of the D-amino acid on the sweetness potency of L-aspartyl-D-amino acid-(S)-α-ethylbenzyl amides.

HOOC—CH₂—C(H)(NH₂)—C(=O)—N(H)—C(R)(H)—C(=O)—N(H)—C(CH₂CH₃)(H)(phenyl) (S)

| R | SP (× sucrose) |
|---|---|
| —CH(CH₃)₂ | 1,500 |
| —CH₂CH₃ | 2,500 |

TABLE 4

Effect of aromatic methylation on the sweetness of (L)-aspartyl-D-alanine-(R,S)-α-methylbenzyl amides.

HOOC—CH₂—C(H)(NH₂)—C(=O)—N(H)—C(CH₃)(H)—C(=O)—N(H)—C(CH₃)(H)(phenyl-R) (R,S)

| R | SP (× sucrose) |
|---|---|
| H | 90 |
| ortho CH₃ | 40 |
| meta CH₃ | 40 |
| para CH₃ | 80 |

The sweetener compounds and the physiologically acceptable salts thereof of the present invention provide advantages as sweetening agents in view of their high sweetness potency, their physical form and stability. They are, ordinarily, crystalline, non-hygroscopic, water soluble solids. They are characterized by possessing a sweet taste, devoid of undesirable harsh or bitter flavor qualities at ordinary use levels.

The compounds of the invention can be prepared in a variety of forms suitable for utilization as sweetening agents. Typical forms that can be employed are solids, such as powders, tablets, granules and dragees, and liquid forms, such as solutions, suspensions, syrups, emulsions, as well as other commonly employed forms that are particularly suited for combination with edible materials. These forms can be comprised of the compounds of the present invention, or of their physiologically acceptable salts, either apart or in association with non-toxic sweetening agent carriers, e.q., non-toxic substances commonly employed in association with sweetening agents. Such suitable carriers include liquids such as water, ethanol, glycerol, corn oil, peanut oil, soybean oil, sesame oil, propylene glycol, corn syrup, maple syrup and liquid paraffin, and solids such as sorbitol, citric acid, lactose, cellulose, starch, dextrin, modified starches, polysaccharides such as polydextrose (see, e.g. U.S. Pat. Nos. 3,766,165 and 3,876,794), calcium phosphate (mono-, di- or tri-basic) and calcium sulfate.

The sweeteners of this invention may be used to provide desirable properties of sweetness in any orally ingestible product. Examples of specifically ingestible materials include: fruits, vegetables, juices, meat products such as ham, bacon and sausage; egg products, fruit concentrates, gelatins and gelatin-like products such as jams, jellies, preserves, and the like; milk products such as ice cream, sour cream and sherbet; icings, syrups including molasses; corn, wheat, rye, soybean, oat, rice and barley products, nut meats and nut products, beverages such as coffee, tea, carbonated and non-carbonated soft drinks, beers, wines and liquors; confections such as candy and fruit flavored drops, condiments such as herbs, spices and seasonings, flavor enhancers such as monosodium glutamate and chewing gum. The sweeteners may also be useful in prepared packaged products such as dietetic sweeteners, liquid sweeteners, granulated flavor mixes which upon reconstitution with water provide non-carbonated drinks, instant pudding mixes, instant coffee and tea, coffee whiteners, malted milk mixes, pet foods, livestock feed, tobacco and personal care products such as mouth washes and toothpaste as well as proprietary and non-proprietary pharmaceutical preparations and other products of the food, pharmaceutical and sundry industries. Because of their high heat stability at pH 7, these sweeteners are adept for baking applications such as powdered baking mixes for the preparation of breads, cookies, cakes, pancakes, donuts and the like. Especially preferred sweetened edible compositions are carbonated beverages containing one or more of the subject sweeteners. The sweeteners could also be used in frozen desserts, chewing gum, dentifrices, medications or any other orally ingestible substance.

The sweeteners of this invention may also be blended with other sweeteners known to the art, such as, for example, sucrose, fructose and other polyols, as well as other high potency non-nutritive sweeteners including but not limited to saccharin, cyclamate, aspartame, acesulfame-K, alitame, sucralose, stevioside and the like, which are useful for sweetening edible materials. Especially useful are the blends of the sweeteners of this invention and saccharin or physiologically acceptable salts thereof. Examples of saccharin salts include the sodium, potassium, calcium and ammonium salts. Examples of the sweeteners of this invention also include their sulfates, malates, hydrochlorides, carbonates, phosphates, citrates, benzoates and the like. In blends with saccharin the compounds of this invention may reduce or completely mask the well known, undesirable bitter aftertaste of the saccharin.

The invention is further illustrated by the following examples.

EXAMPLES

EXAMPLE 1

N-benzyloxycarbonyl-$\beta$-benzyl-L-aspartyl-D-alanine

This example describes the preparation of the protected dipeptide utilized in subsequent examples.

A mixture of 5.0 g N-benzyloxycarbonyl-$\beta$-benzyl-L-aspartic acid (14 mmoles), 100 ml tetrahydrofuran, 2.88 g (14 mmoles) dicyclohexylcarbodiimide and 1.61 g (14 mmoles) N-hydroxysuccinimide were stirred at room temperature overnight. The solution was then filtered and the filtrate evaporated to give a thick oil. To this oil was added 80 ml dioxane followed by a solution of 1.5 g (16.6 mmoles) D-alanine, 10 ml dioxane, 20 ml $H_2O$ and 1.85 ml (1.34 g, 13.3 mmoles) triethylamine.

The mixture was stirred again at room temperature overnight. The solution was filtered and the filtrate concentrated to approximately 25 ml. The residue was diluted with 100 ml $H_2O$, acidified to pH 2.0 with 10% $H_3PO_4$ and extracted twice with 100 ml ethyl acetate. The combined ethyl acetate layers were backwashed with 100 ml $H_2O$ and 50 ml brine. After drying over $Na_2SO_4$ the ethyl acetate layer was evaporated to give a white solid. This was crystallized from ethyl acetate-hexane to give 4.2 g, mp 165°-67° C. A second crop of 303 mg was obtained at 5° C. from the mother liquors to give a total yield of 4.5 g (75%). The literature (U.S. Pat. No. 4,411,925) gives mp 158°-59° C.

N-carbobenzyloxy, B-benzyl-L-aspartyl-D-valine (57%, mp 93°-96° C.); N-carbobenzyloxy-$\beta$-benzyl-L-aspartyl-D-$\alpha$-amino butyric acid (57%, mp 151°-53° C.) [U.S. Pat. No. 4,571,345, mp 150°-52° C.), N-carbobenzyloxy-$\beta$-benzyl-L-aspartyl-D-phenylglycine (54%, mp. 64°-67° C.) and N-carbobenzyloxy-$\beta$-benzyl-L-aspartyl-D-$\alpha$-aminopentanoic acid (73%, mp 91°-95° C.) were prepared in a similar procedure substituting equivalent weights of the appropriate D-amino acid for the D-alanine.

EXAMPLE 2

Synthesis of L-aspartyl-D-alanine-N-(S)-$\alpha$-methyl-benzylamide

In a 50 ml flask was mixed 500 mg (1.17 mmoles) N-benzyloxycarbonyl-$\beta$-benzyl-L-aspartyl-D-alanine, 0.16 ml (150 mg., 1.24 mmoles) (S)-$\alpha$-methyl-benzylamine, 241 mg (1 17 mmoles) dicyclohexylcarbodiimide, 210 mg (1.17 mmoles) N-hydroxy-5-norbornene-2,3-dicarboximide and 25 ml dioxane. The solution was stirred at room temperature overnight and filtered. The filtrate was then evaporated to a solid. This was dissolved in 50 ml ethyl acetate, washed twice with 30 ml, 5% aqueous citric acid, twice with 30 ml 4% aqueous $NaHCO_3$ and twice with 30 ml brine, dried over $MgSO_4$ and evaporated to give 0.66 g white solid. This was recrystallized from ethyl acetate/hexane to give 0.55 g (1.04 mmoles, 89%) white crystals, mp 168°-70° C.

$^1$H NMR (200 MHz, $CDCl_3$), $\delta$: 7.27-7.33 (m,Ar—H, 15H), 7.2 (d,—N—H, 1H), 7.0 (d,—NH, 1H), 6.0 (d, —NH, 1H), 5.07 (s, —O—$CH_2$—, 2H), 5.05 (s, —$OCH_2$—, 2H), 4.4-4.6 (m, N—CH—, 3H), 2.65-3.1 (dd, —$CH_2$—, 2H), 1.4 (d, C—$CH_3$, 3H), 1.3 (d,C—$CH_3$, 3H)

$^{13}$C NMR (50 MHz, $CDCl_3$), $\delta$: 173.6 (—COO—), 173.0 (—CON)—, 172.6 (—CON), 158.0 (—OCON—), 145.6 (—Ar—), 137.9 (—Ar), 137.3 (—Ar), 130.2-130.7 (m, —Ar), 69.3, (—O—$CH_2$—), 68.8 (—$CH_2$—O), 53.4 (Ar—CH—N), 51.1 (—CH—N), 50.7 (—CH—N), 38.1 (—$CH_2$—), 23.8 (—$CH_3$), 19.5 (—$CH_3$)

(b) 0.55 g (1.04 mmoles) N-benzyloxycarbonyl-$\beta$-benzyl-L-aspartyl-D-alanine-(S)-$\alpha$-methyl-benzyl amide was dissolved in 50 ml methanol. To this was added 0.06 g 10% Pd on activated carbon. The mixture was hydrogenated at 40 psi overnight. The catalyst was removed by filtration through a Celite ® filter material (available from Celite Corporation, Lompoc, Calif.) and the filtrate was evaporated to give 0.43 g solid. This was then dissolved in 200 ml water and filtered to remove a small amount of the dicyclohexyl-urea that was carried over. The filtrate was freeze-dried to give 0.26 g (0.85 mmoles, 82%) white solid. mp 194°-96° C. $[\alpha]_D = +41.5°$ (13.0 mg in 1.00 ml methanol).

$^1$H NMR (200 MHz, $CD_3OD$), $\delta$: 7.26-7.4 (m, —Ar—H, 5H), 5.00 (m, N—CH—, 1H), 4.37-4.42 (m, N—CH—, 1H), 3.95-4.1 (m, N—CH—, 1H), 2.60-2.71 (m, —$CH_2$—, 2H), 1.44 (d, —$CH_3$, 3H), 1.38 (d, —$CH_3$, 3H).

$^{13}$C NMR (50 MHz, $D_2O$), $\delta$: 180.5 (CO), 178.7 (CO), 173.8 (CO), 148.0 (Ar), 133.4, 132.0, 130.4 (Ar), 54.9, 54.4, 53.9 (CHN) 41.6 ($CH_2CO$), 25.5 ($CH_3$) and 21.1 ($CCH_3$).

Sweetness—180 times sucrose. (The sweetness potency was determined by comparison, using well known methods, against 200 ppm aspartame solution, adopting for aspartame the sweetness potency value of 180 times sucrose.)

EXAMPLE 3

Synthesis of L-aspartyl-D-$\alpha$-aminobutyric-acid N-(S)-$\alpha$-methylbenzyl amide Following the procedure of Example 2, L-aspartyl-D-$\alpha$-aminobutyric-acid-N-(S)-$\alpha$-methylbenzyl amide was synthesized using N-carbobenzyloxy-$\beta$-benzyl-L- aspartyl-D-α-aminobutyric acid in place of the N-carbobenzyloxy-β-benzyl-L-aspartyl-D-alanine.

Yield of protected intermediate—56%, mp. 142°-46° C.
Yield of sweetener—99%, mp. 176°-78° C.
Sweetness—360 times sucrose

EXAMPLE 4

Synthesis of L-aspartyl-D-α-aminopentanoic-acid-N-(S)-α-methylbenzyl amide

Following the procedure of Example 2, L-aspartyl-D-α-aminopentanoic-acid-N-(S)-α-methylbenzyl amide was synthesized using N-carbobenzyloxy-β-benzyl-L-aspartyl-D-α-amino-pentanoic acid in place of the N-carbobenzyloxy-β-benzyl-L-aspartyl-D-alanine.

Yield of protected intermediate—69%, mp. 158°-61° C.
Yield of sweetener—36%, mp. 203°-05° C.
Sweetness—90 times sucrose

EXAMPLE 5

Synthesis of L-aspartyl-D-valine-N-(S)-α-methylbenzyl amide

Following the procedure of Example 2, L-aspartyl-D-valine-N-(S)-α-methylbenzyl amide was valine in place of the N-carbobenzyloxy-β-benzyl-L-aspartyl-D-alanine.

Yield of protected intermediate—71%, mp. 178°-80° C.
Yield of sweetener—45%, mp. 235° C. (dec.)
Sweetness—540 times sucrose

EXAMPLE 6

Synthesis of L-aspartyl-D-phenylglycine-N-(S)-α-methylbenzyl amide

Following the procedure of Example 2, L-aspartyl-D-phenylglycine-N-(S)-α-methylbenzyl amide was synthesized using N-carbobenzyloxy-β-benzyl-L-aspartyl-D-phenylglycine in place of the N-carbobenzyloxy-β-benzyl-L-aspartyl-D-alanine.

Yield of protected intermediate—46%, mp. 160°-64° C.
Yield of sweetener—44%, mp. 211°-13° C.
Sweetness—270 times sucrose

EXAMPLE 7

Synthesis of L-aspartyl-D-alanine-N-(R)-α-methylbenzyl amide

Following the procedure of Example 2, L-aspartyl-D-alanine-N-(R)-α-methylbenzyl amide was synthesized using (R)-α-methylbenzyl amine in place of the (S)-isomer.

Yield of protected intermediate—88%, mp. 167°-69° C.
Yield of sweetener—82% mp. 198°-200° C.
Sweetness—less than 10 times sucrose

EXAMPLE 8

Synthesis of L-aspartyl-D-alanine-N-(R,S)-α-ethylbenzyl amide

Following the procedure of Example 2, L-aspartyl-D-alanine-N-(R,S)-α-ethylbenzyl amide was synthesized using (R,S)-α-ethylbenzyl amine in place of (S)-α-methylbenzyl amine.

Yield of protected intermediate—86%, mp 133°-34.5° C.
Yield of sweetener—87%, mp. 180°-83°
Sweetness—270 times sucrose

EXAMPLE 9

Synthesis of L-aspartyl-D-alanine-N-(R,S)-α-isopropylbenzyl amide

Following the procedure of Example 2, L-aspartyl-D-alanine-N-(R,S)-α-isopropylbenzyl amide was synthesized using (R,S)-α-isopropyl-benzylamine in place of (S)-α-methylbenzylamine.

Yield of protected intermediate—78%, mp. 135°-39° C.
Yield of sweetener—90%, mp. 187°-91° C.
Sweetness—180 times sucrose

EXAMPLE 10

Synthesis of L-aspartyl-D-alanine-N-(R,S)-α-t-butylbenzyl amide

Following the procedure of Example 2, L-aspartyl-D-alanine-N-(R,S)-α-t-butylbenzyl amide was synthesized using (R,S)-α-t-butylbenzylamine in place of (S)-α-methylbenzylamine.

Yield of protected intermediate—77%, mp. (amorphous)
Yield of sweetener—90%, mp. 158°-63° C.
Sweetness—150 times sucrose

EXAMPLE 11

Synthesis of L-aspartyl-D-alanine-N-(R,S)-α-n-propylbenzyl amide

Following the procedure of Example 2, L-aspartyl-D-alanine-N-(R,S)-α-n-propylbenzyl amide was synthesized using (R,S)-α-n-propylbenzylamine in place of (S)-α-methylbenzyl amine.

Yield of protected intermediate—84%, mp. 153°-55° C.
Yield of sweetener—83% mp. 184°-6° C.
Sweetness—90 times sucrose

EXAMPLE 12

Synthesis of L-aspartyl-D-alanine-N-α-phenyl benzyl amide

Following the procedure of Example 2, L-aspartyl-D-alanine-N-α-phenyl benzyl amide was synthesized using α-phenylbenzylamine in place of (S)-α-methylbenzylamine.

Yield of protected intermediate—83% mp. 165°-68° C.
Yield of sweetener—51%, mp. 193°-95° C.
Sweetness—180 times sucrose

EXAMPLE 13

Synthesis of L-aspartyl-D-alanine-N-α-cyclopropyl benzyl amide

Following the procedure of Example 2, L-aspartyl-D-alanine-N-α-cyclopropyl benzyl amide was synthesized using (R,S)-α-cyclopropyl benzyl amine in place of (S)-α-methylbenzylamine.

Yield of protected intermediate—62%, mp. 162°-6° C.
Yield of sweetener—93%, mp. 188°-90° C.
Sweetness—1,080 times sucrose

EXAMPLE 14

Synthesis of L-aspartyl-D-α-aminobutyric acid-N-(S)-α-ethylbenzyl amide (a)

N-carbobenzyloxy-β-benzyl-L-aspartyl-D-α-aminobutyric acid-(S)-α-ethyl benzyl amide To 250 ml 4% aqueous sodium carbonate was added 3.22 g (11.3 mmoles) (S)-α-ethylbenzyl amine L-(+)-tartrate (mp. 176°–79° C.). The mixture was extracted twice with 25 ml methylene chloride, the combined methylene chloride extracts dried over $Na_2SO_4$ and evaporated at <25° C. and 20 mm to give a liquid. This was dissolved in 10 ml dioxane and added to a stirred mixture of 5.0 g (11.3 mmoles) N-carbobenzyloxy-β-benzyl-L-aspartyl-D-α-amino butyric acid, 200 ml dioxane, 2.5 g (12.1 mmoles) dicyclohexylcarbodiimide and 1.25 g (7.0 mmoles) N-hydroxy-5-norbornene 2,3-dicarboximide. The mixture was stirred at room temperature overnight, then filtered and the filtrate evaporated to a thick oil. The oil was dissolved in 300 ml chloroform and washed twice with 200 ml 4% aqueous citric acid, three times with 150 ml 4% aqueous $NaHCO_3$ and with 100 ml $H_2O$. Drying the chloroform layer over $Na_2SO_4$ and evaporation of the solvent gave an amorphous solid. Crystallization from ethyl acetate and hexane yielded 5.55 g (9.93 mmoles, 88%) of the protected sweetener, mp. 134°–36° C.

(b)

L-aspartyl-D-α-amino-butyric-acid-N-(S)-α-ethylbenzyl amide

To a solution of 5.25 g (9.4 mmoles) of the product of step (a), described above, in 100 ml methanol was added 400 mg of 10% Pd/C catalyst and the mixture hydrogenated at 40 psi $H_2$ on a Parr shaker for 3 hours at room temperature. The catalyst was removed by filtration through a bed of a Celite ® filter material and the filtrate evaporated to give a white solid. This was crystallized from 95% ethanol and acetonitrile to give 1.56 g (4.66 mmoles, 49.6% mp. 197°–98° C.) of L-aspartyl-D-α-amino-butyric-acid-N-(S)-α-ethylbenzyl amide. A second crop was also obtained: 0.397 g (1.18 mmoles, 12.6%, mp 195°–97° C.).

$^1$H NMR (200 MHZ, $CD_3OD$) δ: 7.2 (m, ArH, 5H): 4.60 (m, —N—C$\underline{H}$(R)CO—, 1H), 4.20 (m, —NC$\underline{H}$(R)(CO), 1H), 3.94 (m, —C$\underline{H}$(R) Ar, 1H), 2.5 (m, C$\underline{H}_2$—$CO_2H$, 2H), 1.55–1.85 (m, C$\underline{H}_2$, 4H) and 0.83 (2t, $\overline{CH_3}$, 6H).

$^{13}$C NMR (50 MHz, $CD_3OD$) δ: 175.1, 178.2 and 180.9 (CO), 132.3, 132.6, 134.0, 148.7 (Ar), 61.1 (NHC$\underline{H}$(R)Ar), 60.7 (NHCHCO), 56.7 (NCHCO), 42.8 (C$\underline{H}_2$CO), 34.7 ($CH_2$), 31.$\overline{3}$ ($CH_2$), 15.8 (C$\overline{H}_3$), and 15.0 ($\overline{CH}_3$).

Sweetness—2500×Sucrose

EXAMPLE 15

Synthesis of L-aspartyl-D-valine-N-(S)-α-ethylbenzyl amide

Following the procedure of Example 14, L-aspartyl-D-valine-N-(S)-α-ethylbenzyl amide was synthesized using N-carbobenzyloxy-β-benzyl-L-aspartyl-D-valine in place of N-carbobenzyloxy-β-benzyl-L-aspartyl-D-α-aminobutyric acid.

Yield of protected intermediate—54%, mp. 167°–71° C.

Yield of sweetener—42%, mp. 221°–22° C.

Sweetness—1500 times sucrose.

EXAMPLE 16

Cola Beverage

L-aspartyl-D-α-aminobutyric acid-N-(S)-ethylbenzylamide (0.16 g) is dissolved in 500 ml water and the volume adjusted to one liter. Citric acid (1 g), phosphoric acid (2 g), caramel color (10 g), cola flavoring (10 g) and a benzoate preservative (2 g) are dissolved in the liter solution of sweetener. The resulting cola concentrate is diluted with 3 liters of water to provide a single strength beverage. Carbonation produces a satisfying effervescent carbonated cola drink having a palatable sweetness.

EXAMPLE 17

Citrus Beverage 160 mg of L-aspartyl-D-α-aminobutyric-acid-N-(s)-α-ethylbenzylamide is dissolved in 1 liter of water. To this 4.5 g citric acid, 2 g sodium benzoate and 10 g of citrus flavoring are added. The resulting citrus concentrate is diluted with 3 liters of water to provide a single strength beverage. Carbonation as desired gives a satisfactory effervescent beverage having a palatable sweetness.

EXAMPLE 18

Dietetic Hard Candy

A hard candy is prepared according to the following formulation and procedure:

| Ingredients | % by weight (approximate) |
| --- | --- |
| A sweetener | — |
| FD and C Red #40 (10% aqueous) | 0.05 |
| Cherry Flavor | 0.1 |
| Citric acid | 1.0 |
| Polydextrose* | 70 |
| Water | 30 |

*U.S. Pat. No. 3,766,165

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

In a small beaker dissolve the sweetener in water, add color, flavor and citric acid and mix well to dissolve. In a separate beaker combine polydextrose and water. Stir while heating to 140° C., then allow to cool to 120°–125° C. Add other ingredients from a small beaker and mix or knead thoroughly. Transfer the material to an oil coated marble slab and allow to cool to 75°–80° C. Extract the material through an oil coated impression roller.

EXAMPLE 19

Gelatin Dessert

A gelatin dessert is prepared according to the following composition and procedure.

| Ingredients | % by weight (approximate) |
| --- | --- |
| Gelatin 225 Bloom | 1.5 |
| Citric acid | 0.36 |
| Sodium citrate | 0.26 |

| Ingredients | % by weight (approximate) |
|---|---|
| Strawberry flavor | 0.06 |
| A sweetener | — |
| Boiling water | 49 |
| Cold Water | 49 |

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

Premix the first five ingredients, add to boiling water and stir to dissolve completely. Add cold water and stir briskly. Transfer to serving dishes and refrigerate until set.

EXAMPLE 20

Low Calorie Table Sweetener

Low calorie table sweeteners are prepared according to the following formulations:

A. A powder form of sweetener is prepared by blending the following ingredients.

| Ingredients | % by weight (approximate) |
|---|---|
| A sweetener | — |
| Crystalline sorbitol | 49.5 |
| Dextrim (dextrose equivalent 10) | 50 |
| Monosodium glutamate | 0.02 |
| Glucomo-delta-lactone | 0.02 |
| Sodium Citrate | 0.02 |

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

B. A table sweetener in liquid form is prepared as follows.

| Ingredients | % by weight (approximate) |
|---|---|
| A sweetener | — |
| Water | 99 |
| Sodium benzoate | 0.10 |

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

EXAMPLE 21

Frozen Dessert

A vanilla sugarless frozen dessert is prepared according to the following formulation by conventional practice.

| Ingredients | % by weight (approximate) |
|---|---|
| Heavy cream (35% butterfat) | 23 |
| Nonfat milk solids | 10 |
| Mono- and diglyceride emulsifier | 0.25 |
| Polydextrose* | 11 |
| Water | 54 |
| A sweetener | 0.06 |
| Gelatin (225 Bloom) | 0.5 |

*U.S. Pat. No. 3,766,165

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

EXAMPLE 22

Canned Pears

Fresh Pears are washed, peeled, cored, sliced into pieces and immersed in an aqueous solution containing 0.05% by weight of ascorbic acid. The sliced fruit is packed into screw-cap jars and the jars filled with a syrup containing the following ingredients:

| Ingredients | % by weight (approximate) |
|---|---|
| Sorbitol | 25 |
| A sweetener | — |
| Citric acid | 0.12 |
| Water | 75 |

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

The jars are capped loosely and placed in an autoclave containing hot water and processed at 100° C. for minutes. The jars are removed, immediately sealed by tightening the caps and allowed to cool.

EXAMPLE 23

Powder Beverage Concentrate

| Ingredients | % by weight (approximate) |
|---|---|
| Citric acid | 32 |
| Sodium citrate | 5 |
| Strawberry flavor | 58 |
| Strawberry FD and C color | 0.5 |
| A sweetener | — |
| Carboxymethyl cellulose | 2.4 |

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

Combine all ingredients in a blender and blend until homogeneous. For use, 1.73 g. of powder beverage concentrate is dissolved in 4 fluid ounces (118 ml.) of water.

EXAMPLE 24

Baked Cake

A vanilla cake may be prepared employing the following recipe:

| Ingredients | % by weight (approximate) |
| --- | --- |
| Emulsified shortening | 7.9 |
| Water | 9.9 |
| Eggs | 11.3 |
| Sodium bicarbonate | 0.5 |
| Vanilla extract, single fold | 0.1 |
| Glucono-delta-lactone | 0.8 |
| Polydextrose*, 70% aqueous solution | 39.5 |
| Nonfat dry milk | 1.2 |
| Cake flour | 27.6 |
| Whole milk powder | 0.4 |
| Wheat starch | 0.7 |
| A sweetener | — |

*U.S. Pat. No. 3,766,165

The sweetener is an L-aspartyl-D-α-aminoalkanoyl-(S)-N-α-alkylbenzyl amide as disclosed herein, e.g. L-aspartyl-D-α-aminobutyric acid-S-α-ethylbenzyl amide or L-aspartyl-D-valine-S-α-ethylbenzyl amide. The quantity of sweetener added is varied depending on the sweetness potency of the sweetener.

Combine nonfat dry milk, whole milk powder, polydextrose solution and emulsified shortening. Mix at low speed until creamy and smooth (about 3 minutes), add eggs and beat until a homogeneous creamy mix is obtained. Dissolve sweetener in water, add to creamy homogenate and mix 2–3 minutes. Add remaining ingredients and mix until creamy and smooth (3–5 minutes). Place 120 g. of batter in small pregreased pan and bake at 350° F. (176° C.) for 30 minutes.

What is claimed is:

1. An artificial sweetener compound comprising an L-aspartyl-D-α-aminoalkanoyl-(S)-α-alkylbenzyl amide having the structure:

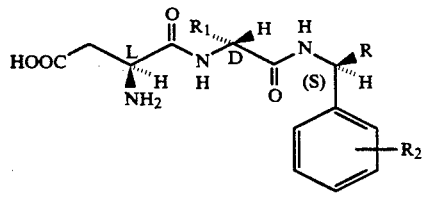

wherein
$R_1 = H$, $-CH_3$, $-CH_2CH_3$, $-CH_2CH_2CH_3$, $-CH(CH_3)_2$, $-C(CH_3)_3$, $-CH_2OCH_3$, $-CH_2OH$ or phenyl wherein $R_2 = H$ or $CH_3$;

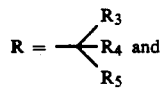

$R_3$, $R_4$ and $R_5 = H$, $-CH_3$ or $-CH_2CH_3$; or

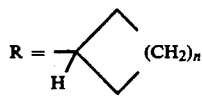

wherein n=0, 1, 2, 3, 4.

2. The artificial sweetener compound of claim 1 wherein $R_1 = -CH_2CH_3$, $R_3 = -CH_3$ and $R_2 = R_4 = R_5 = H$.

3. The artificial sweetener compound of claim 1 wherein $R_1 = -CH_2(CH_3)_2$, $R_3 = -CH_3$ and $R_2 = R_4 = R_5 = H$.

4. An edible composition comprising an edible material and an artificial sweetener compound according to claim 1.

5. The edible composition of claim 4 wherein the edible composition is selected from the group consisting of a cola beverage, a citrus beverage, a baked cake, a dietetic hard candy, a gelatin dessert, a low calorie table sweetener, a frozen dessert, canned pears, and a powder beverage concentrate.

6. A method of sweetening an edible composition comprising adding an artificial sweetener compound according to claim 1 to an edible material to produce a sweetened edible composition.

7. An artificial sweetener compound selected from the group consisting of L-aspartyl-D-α-aminobutyric-acid-(S)-N-α-ethylbenzyl amide, L-aspartyl-D-valine-(S)-N-α-ethylbenzyl amide, L-aspartyl-D-alanine-N-(S)-α-methylbenzyl amide, L-aspartyl-D-α-aminobutyric-acid-N-(S)-α-methylbenzyl amide, L-aspartyl-D-α-aminopentanoic-acid-N-(S)-α-methylbenzyl amide, L-aspartyl-D-valine-N-(S)-α-methylbenzyl amide, L-aspartyl-D-phenylglycine-N-(S)-α-methylbenzyl amide, L-aspartyl-D-alanine-N-(R,S)-α-ethylbenzyl amide, L-aspartyl-D-alanine-N-(R,S)-α-isopropylbenzyl amide, L-aspartyl-D-alanine-N-(R,S)-α-t-butylbenzyl amide, L-aspartyl-D-alanine-N-(R,S)-α-n-propylbenzyl amide, L-aspartyl-D-alanine-N-α-phenyl benzyl amide and L-aspartyl-D-alanine-N-α-cyclopropyl benzyl amide.

8. An artificial sweetener compound comprising L-aspartyl-D-α-aminobutyric-acid-(S)-N-α-ethylbenzyl amide.

9. An artificial sweetener compound comprising L-aspartyl-D-valine-(S)-N-α-ethylbenzyl amide.

10. An artificial sweetener compound comprising L-aspartyl-D-alanine-N-(S)-α-methyl-benzyl amide.

11. An artificial sweetener compound comprising L-aspartyl-D-α-aminobutyric-acid-N-(S)-α-methylbenzyl amide.

12. An artificial sweetener compound comprising L-aspartyl-D-α-aminopentanoic-acid-N-(S)-α-methylbenzyl amide.

13. An artificial sweetener compound comprising L-aspartyl-D-valine-N-(S)-α-methylbenzyl amide.

14. An artificial sweetener compound comprising L-aspartyl-D-phenylglycine-N-(S)-α-methylbenzyl amide.

15. An artificial sweetener compound comprising L-aspartyl-D-alanine-N-(R,S)-α-ethylbenzyl amide.

16. An artificial sweetener compound comprising L-aspartyl-D-alanine-N-(R,S)-α-isopropylbenzyl amide.

17. An artificial sweetener compound comprising L-aspartyl-D-alanine-N-(R,S)-α-t-butylbenzyl amide.

18. An artificial sweetener compound comprising L-aspartyl-D-alanine-N-(R,S)-α-n-propylbenzyl amide.

19. An artificial sweetener compound comprising L-aspartyl-D-alanine-N-α-phenyl benzyl amide.

20. An artificial sweetener compound comprising L-aspartyl-D-alanine-N-α-cyclopropyl benzyl amide.

21. A method of sweetening an edible composition comprising adding the blend of an artificial sweetener compound according to claim 1 and of sucrose to an edible material to produce a sweetened edible composition.

22. A method of sweetening an edible composition comprising adding the blend of an artificial sweetener compound according to claim 1 and of fructose to an edible material to produce a sweetened edible composition.

23. A method of sweetening an edible composition comprising adding the blend of an artificial sweetener compound according to claim 1 and of saccharin to an edible material to produce a sweetened edible composition.

24. A method of sweetening an edible composition comprising adding the blend of an artificial sweetener compound according to claim 1 and of cyclamate to an edible material to produce a sweetened edible composition.

25. A method of sweetening an edible composition comprising adding the blend of an artificial sweetener compound according to claim 1 and of aspartame to an edible material to produce a sweetened edible composition.

26. A method of sweetening an edible composition comprising adding the blend of an artificial sweetener compound according to claim 1 and of acesulfame-K to an edible material to produce a sweetened edible composition.

27. A method of sweetening an edible composition comprising adding the blend of an artificial sweetener compound according to claim 1 and of alitame to an edible material to produce a sweetened edible composition.

28. A method of sweetening an edible composition comprising adding the blend of an artificial sweetener compound according to claim 1 and of sucralose to an edible material to produce a sweetened edible composition.

29. A method of sweetening an edible composition comprising adding the blend of an artificial sweetener compound according to claim 1 and of stevioside to an edible material to produce a sweetened edible composition.

30. An edible composition comprising adding the blend of an artificial sweetener compound according to claim 1 and of a sweetener selected from the group consisting of sucrose, fructose, saccharin, cyclamate, aspartame, acesulfame-K, alitame, sucralose and stevioside to an edible material to produce a sweetened edible composition.

* * * * *

UNITED STATES PATENT AND TRADEMARK OFFICE
CERTIFICATE OF CORRECTION

PATENT NO. : 5,286,509

DATED : February 15, 1994

INVENTOR(S) : D'Angelo, et al

It is certified that error appears in the above-indentified patent and that said Letters Patent is hereby corrected as shown below:

Column 2, lines 31 and 32, "—CH-$_2$OH" should read ——CH$_2$OH——.

Column 3, line 28 "B-" should be --$\beta$- --;

Column 4, line 41, "B-" should be --$\beta$- --:

Column 9, line 61, "B-" should be -- $\beta$- --.

Column 17, lines 49 and 50, "----CH-$_2$OH" should read --CH$_2$OH--.

This certificate supersedes Certificate of Correction issued September 26, 1995.

Signed and Sealed this

Ninth Day of April, 1996

Attest:

BRUCE LEHMAN

Attesting Officer

Commissioner of Patents and Trademarks